(12) United States Patent
Kunc et al.

(10) Patent No.: US 7,954,741 B2
(45) Date of Patent: Jun. 7, 2011

(54) APPARATUS FOR GRINDING BIOLOGICAL SAMPLES

(75) Inventors: Thierry Kunc, Versailles (FR);
Jean-Jacques Bougy, Garancieres (FR);
Jean Boquet, Le Perray En Yvelines (FR); Julien Vallayer, Magny les Hameaux (FR); Emmanuelle Sorel, Rouvres (FR)

(73) Assignee: Bertin Technologies (FR)

( * ) Notice: Subject to any disclaimer, the term of this patent is extended or adjusted under 35 U.S.C. 154(b) by 66 days.

(21) Appl. No.: 12/306,073

(22) PCT Filed: Jun. 28, 2007

(86) PCT No.: PCT/FR2007/001094
§ 371 (c)(1),
(2), (4) Date: Feb. 11, 2009

(87) PCT Pub. No.: WO2008/000962
PCT Pub. Date: Jan. 3, 2008

(65) Prior Publication Data
US 2009/0206187 A1  Aug. 20, 2009

(30) Foreign Application Priority Data
Jun. 30, 2006 (FR) ..................... 06 05944

(51) Int. Cl.
*B02C 19/00* (2006.01)

(52) U.S. Cl. .................................. 241/65; 241/2
(58) Field of Classification Search ............... 241/2, 23, 241/65, 66, 67
See application file for complete search history.

(56) References Cited

U.S. PATENT DOCUMENTS

| | | | |
|---|---|---|---|
| 3,172,546 A * | 3/1965 | Schreiner | 241/23 |
| 3,534,914 A * | 10/1970 | Chaplenko | 241/66 |
| 4,295,613 A | 10/1981 | Moore et al. | |
| 5,577,837 A | 11/1996 | Martin et al. | |
| 6,235,501 B1 | 5/2001 | Gautsch et al. | |
| 6,695,236 B2 * | 2/2004 | Gazeau | 241/2 |

FOREIGN PATENT DOCUMENTS

| | | |
|---|---|---|
| DE | 297 06 031 U1 | 8/1997 |
| DE | 197 55 960 C1 | 11/1998 |
| FR | 2 858 057 A1 | 1/2005 |
| WO | WO 89/09437 | 10/1989 |

OTHER PUBLICATIONS

International Search Report for PCT/FR2007/001094, filed Jun. 28, 2007.

* cited by examiner

*Primary Examiner* — Mark Rosenbaum
(74) *Attorney, Agent, or Firm* — Alston & Bird LLP

(57) ABSTRACT

Apparatus for grinding biological samples contained in tubes (12) carried by a turntable (10) driven with oscillating motion, the zone in which the tubes (12) oscillate being surrounded by cooling means (30) enabling the samples in the tubes (12) to be maintained at a desired low temperature, e.g. 4° C., while they are being ground.

13 Claims, 3 Drawing Sheets

APPARATUS FOR GRINDING BIOLOGICAL SAMPLES

The invention relates to apparatus for grinding biological samples, the apparatus comprising a turntable for supporting tubes containing samples and means for driving the turntable with oscillating motion about a center of rotation situated on the axis of the turntable.

Such an apparatus is described in particular in documents WO-A-2004/012851 and FR-A-2 872 233 and comprises concentric bearings mounted one inside the other to support and center the tube-carrier turntable, the bearings being disposed between an elastically suspended portion of the apparatus and a drive shaft carrying the turntable.

The turntable is prevented from rotating about the drive shaft so that the tubes containing the samples are subjected to curvilinear reciprocating motion at high frequency and the samples they contain are ground and homogenized by microbeads, e.g. made of glass or ceramic, that are contained together with the samples in the tubes.

That type of grinding is very effective and very fast, but it suffers from the drawback of significantly increasing the temperature of the samples in the tubes. Even when the tubes containing the samples are cooled down prior to grinding, the temperature of the samples at the end of grinding can reach or exceed values of the order of 60° C. to 70° C., which values certain characteristics of the samples are modified in irreversible manner. This applies for example to proteins where protein activity is determined both by the sequence of the protein and also by its three-dimensional structure, which structure is destroyed by heating.

A particular object of the present invention is to provide a solution to this problem that is simple, effective, and satisfactory.

To this end, the invention provides apparatus for grinding biological samples, the apparatus comprising a turntable for supporting tubes containing the samples and means for imparting oscillating motion to the turntable about a center of rotation situated on the axis of the turntable, the apparatus being characterized in that tube cooling means are carried by a portion of the apparatus and surround the above-mentioned turntable to define a cooled zone containing the zone in which the tubes carried by the turntable oscillate.

The cooling means may be fixed or removable, and they serve to maintain the samples at a temperature of a few degrees above zero at the end of grinding, such that the three-dimensional structure of the proteins contained in the samples is not spoilt.

In a preferred embodiment of the invention, the cooling means comprise an annular wall substantially in the shape of a bowl that defines said cooled zone and that includes means for bearing against or fastening to a portion of the apparatus.

When it is put into place on the apparatus, the annular wall may be at a temperature that is well below that of the tubes, and for example below 0° C., so as to absorb the heat radiated by the tubes carried by the turntable, this absorption being sufficient to ensure that, at the end of grinding, the samples contained in the tubes are maintained at a temperature of about 4° C., for example.

In a variant, the annular wall may be fitted with means for feeding or circulating a cooling fluid.

In particular, the wall may be fitted with ducts for circulating a cryogenic gas such as nitrogen, and with ejection nozzles enabling the tubes to be cooled locally by jets of cold gas.

In another variant, the annular wall may be fitted with thermoelectric cooling means that generate low temperature by the Peltier effect.

Advantageously, the cooling means of the invention comprise means for sucking out the gas that has been heated and that is present in the cooled zone that includes the zone in which the tubes carried by the turntable oscillate.

Continuous or discontinuous suction of the gas present in said zone improves performance in terms of keeping the tubes at a desired low temperature.

The apparatus of the invention may also include an accessory of the automatic multiple clamp type for simultaneously picking up a plurality of tubes placed on a common support, said plurality of tubes being transported and deposited simultaneously in housings provided in the turntable of the apparatus, the tubes being picked up automatically by snap-fastening, and the tubes being deposited by performing a single action on a control member provided on the accessory.

It is important for the tubes that are cooled prior to grinding to be put into place on the turntable of the apparatus in a length of time that is as short as possible in order to avoid them warming up again in part prior to grinding.

The accessory of the invention enables all of the tubes that are to be put into place on the turntable (e.g. 24 tubes) to be grasped simultaneously and enables them to be placed simultaneously in their housings in the turntable.

In a preferred embodiment, the accessory comprises a circular cover designed to cover the top ends of the tubes for grasping, and fitted with a plurality of snap-fastener means designed to engage and clamp onto the ends of the tubes, together with a control member formed by a pushbutton or by a quarter-turn button, for example, mounted on the cover and designed to act simultaneously on all of the snap-fastener means to open and allow the ends of the tubes to be released.

This accessory greatly facilitates use of the apparatus of the invention.

The invention can be better understood and other details, characteristics, and advantages thereof appear more clearly on reading the following description made by way of example with reference to the accompanying drawings, in which:

FIG. 1 is a diagrammatic axial section view of an apparatus of the invention;

FIG. 2 is a diagrammatic view on a larger scale showing a portion of the FIG. 1 apparatus;

FIG. 3 shows a variant embodiment of the invention;

FIGS. 4 and 5 are a diagrammatic section view and perspective view of the tube-pickup accessory;

FIG. 6 is a diagrammatic perspective view of a tube support; and

FIGS. 7a, 7b, and 7c are diagrammatic views showing the operation of the tube-pickup accessory.

The grinder apparatus of the invention, as shown diagrammatically in FIGS. 1 and 2, is of the type described in document FR-A-2 872 233, and it essentially comprises a turntable 10 carrying sample tubes 12 at its periphery and mounted at the end of a shaft 14 that is driven in oscillating motion about a center of rotation situated on the axis of the shaft, by an electric motor 16 via an eccentric drive 18.

The shaft 14 is supported and centered on an elastically suspended portion 20 of the apparatus by means of a system of concentric bearings mounted one within another, comprising a ball-and-socket joint with ball bearings carried by the shaft 14 and rotating inside two ball bearings that are axially superposed as described in document FR-A-2 872 233.

As shown in FIG. 1, the apparatus further comprises a pivoting cover 22 carried by a stationary body 24 and covering the turntable 10 while in use for grinding samples contained in the tubes. Locking means 26 enable the cover 22 to be held in the position shown in FIG. 1 while the samples are being ground.

During such grinding, the turntable 10 is prevented from turning about the axis of the shaft 14 and the tubes 12 are driven to perform curvilinear reciprocating motion as represented by arrows in FIG. 2.

In order to prevent the samples contained in the tubes 12 being raised to a high temperature during grinding by the microbeads of glass, ceramic, or any other suitable material that are contained in the tubes, the invention provides for placing cooling means 30 around the zone in which the tubes 12 oscillate, the cooling means comprising a bowl-shaped annular wall 32 carried by a baseplate 34 enabling it to be positioned on and fastened to the elastically suspended portion 20 of the apparatus.

The baseplate 34 also constitutes a chamber communicating with the space defined by the wall 32 and that is fitted with air suction means, comprising in particular a suction duct 36 opening out into the inside of the baseplate at one end and having its opposite end designed for connection to suction means.

In a first embodiment, the cooling means 30 are made of a material that preferably presents relatively high thermal inertia, and they can be taken to a low temperature, e.g. of the order of −60° C. to −100° C., by appropriate means, prior to being placed subsequently in the grinding apparatus on the portion 20 of said apparatus, as shown in FIG. 2, immediately before beginning to grind a series of samples.

The wall 32 then acts as a cold sink for radiant energy from the entire zone in which the tubes 12 carried by the turntable 10 oscillate, thereby enabling the samples to be maintained at a temperature having a value of about 4° C., for example, until the end of grinding.

The air contained inside the wall 32 heats up progressively during sample grinding and it is sucked out by means of the duct 36 in order to enhance sample cooling.

In this embodiment, it is advantageous for the cooling means 30 to be suitable for being put into place on the apparatus and withdrawn from the apparatus in a manner that is simple and fast. For this purpose, they may be fitted with fastener means for engaging the apparatus that are of the rapid screw fastening, bayonet, snap-fastening, etc. type.

In another embodiment of the invention, the wall 32 of the cooling means is fitted with ducts or channels 38 for circulating a cold fluid, thereby enabling the temperature of the wall 32 to be maintained at a desired low value, e.g. lying in the range −60° C. to −100° C. The cold fluid may be a cryogenic gas, such as nitrogen, and the channels 38 may be fitted with nozzles 39 for ejecting cold gas against the tubes.

Under such circumstances, the cooling means 30 may be permanently fastened to the suspended portion 20 of the apparatus and they may be fed with cold fluid solely for sample-grinding operations.

In another embodiment, the wall 32 and the cooling means may be fitted with thermoelectric elements for generating low temperature by the Peltier effect.

Under such circumstances, the cooling means 30 can also be permanently mounted on the portion 20 of the apparatus, with their thermoelectric elements being electrically powered during sample-grinding operations.

In the variant embodiment of FIG. 3, the means for cooling the tubes comprise a bell 132 fastened inside the cover 22 of the apparatus, substantially at the center of said cover, so as to cover the turntable 10 and the tubes 12 once the cover has been lowered into its service position and is held in place by the locking means 26.

In this position, the bottom edge of the bell 132 bears against the elastically suspended portion 20 of the apparatus.

The bell 132 has a cylindrical double wall. The annular gap 134 defined by said double wall is connected to means 136 for delivering or circulating cold air, taken from the rear portion of the cover 22. The inside wall of the bell 132 has a plurality of cold air outlet perforations 138, enabling the tubes 12 to be maintained at a desired temperature while the samples are being ground.

The air inside the bell 132 that is heated on coming into contact with the tubes 12 is exhausted to the outside of the cover via a channel 140 formed in the central top portion of the cover and the bell.

By way of example, the cold air delivered by the means 136 is at a temperature of −50° C. and the temperature inside the bell while in operation is about −20° C.

When the turntable 10 of the apparatus is to receive a certain number of sample tubes 12, e.g. 24 tubes in one particular embodiment of the apparatus, it is advantageous for it to be possible to put the tubes 12 into place on the turntable 10 very quickly.

To do this, the invention proposes an accessory as shown in FIGS. 4 and 5, designed to grasp sample tubes that are placed on a support as shown in FIG. 6.

By way of example, the support 40 is cylindrical in shape and has as many sample tube housings 42 as the turntable 10 of the grinder apparatus.

The housings 42 of the support 40 are disposed in the same manner as the housings for the tubes 12 in the apparatus 10 and they are distributed on a circle having the same diameter as the circle formed by the housings for tubes in the turntable 10.

These housings 42 have depth that is shorter than the length of the tubes 12, such that the top ends of the tubes can project clearly from the housings 42 in order to enable them to be grasped easily by means of the accessory 44 shown in FIGS. 4 and 5.

This accessory essentially comprises an annular cover 46 fitted with a certain number of means 48 for gripping the top ends of the tubes by resilient snap-fastening.

These grip means 48 are connected to a common control member 50, such as a pushbutton, for example, and carried by a central knob 52 on the cover 46.

The operation of the accessory 44 is shown diagrammatically in FIGS. 7a, 7b, and 7c.

FIG. 7a shows a tube 12 being picked up by the means 48.

This can be done merely by placing the accessory 44 above the tubes 12 placed in the housings 42 of the support 40, and then lowering the accessory 44 onto the tubes so as to engage the pickup means 48 on the stoppers 54 of the tubes.

By continuing to push downwards, the elastic snap-fastener means 48 are engaged under the stoppers 54 of the tubes, as shown in FIG. 7b.

It then suffices to lift the accessory 44 so as to extract the tubes 44 from the support 40 and then position in alignment with their housings in the turntable 10 of the grinder apparatus.

When the tubes 12 are engaged in the housings, pressure applied to the pushbutton 50 in the knob 52 serves to release all of the tubes 12 by moving apart the elastic snap-fastener means 48.

For this purpose, and as shown in FIG. 7c, the pushbutton 50 can be associated with means 56 that pushes against the stoppers 54 of the tubes so as to expel them downwards while elastically splaying a passage through the elastic snap-fastener means 48.

Other means could be used in a variant, for example a handle that turns through one-fourth of a turn, or any other suitable means.

The support 40 and the accessory 44 enable the sample tubes 12 to be stored in a cold location, for example at a temperature of 0° C. or a temperature very slightly higher than that, and then enables all of the tubes 12 to be placed in their housings in the turntable 10 in a few seconds, without leaving them enough time to be warmed by the ambient atmosphere.

The accessory 44 avoids any need for an operator to handle the tubes 12 one by one by hand in order to put them into place on the turntable 10 of the apparatus.

The invention claimed is:

1. Apparatus for grinding biological samples, the apparatus comprising a turntable for supporting tubes containing the samples and means for imparting oscillating motion to the turntable about a center of rotation situated on the axis of the turntable, wherein tube cooling means comprise an annular wall substantially in the shape of a bowl or a bell which is positioned or fastened on a stationary portion of the apparatus or on a closable cover of the apparatus, the annular wall surrounding the above-mentioned turntable to define a cooled zone containing the zone in which the tubes carried by the turntable oscillate.

2. Apparatus according to claim 1, wherein said annular wall is at a temperature lower than the temperature of the tubes in order to absorb the heat given off by the tubes.

3. Apparatus according to claim 2, wherein said annular wall is at a temperature lower than 0° C.

4. Apparatus according to claim 1 wherein said annular wall includes means for delivering or circulating a cold fluid.

5. Apparatus according to claim 4, wherein the circulation means are fitted with nozzles for ejecting cold gas against the tubes.

6. Apparatus according to claim 1 wherein said annular wall includes thermoelectric cooling means.

7. Apparatus according to claim 1, wherein the cooling means include means for sucking out the gas that has been heated that is present inside the cooling means.

8. Apparatus according to claim 1, wherein the cooling means are mounted in fixed or removable manner on the stationary portion of the apparatus.

9. Apparatus according to claim 1, wherein the cooling means comprise a bell fastened inside the closable cover of the apparatus, together with means for delivering cold air to the inside of the bell.

10. Apparatus according to claim 9, wherein the bell is double-walled, its inner wall including cold air outlet perforations.

11. Apparatus according to claim 9 wherein an air exhaust channel is formed in a top central portion of the bell and the cover.

12. Apparatus according to claim 1, including an accessory of the automatic multiple clamp type for simultaneously picking up a plurality of tubes placed on a support, in order to transport said plurality of tubes and place the tubes simultaneously in housings provided in the turntable of the apparatus, the tubes being picked up automatically by elastic snap-fastening, and being deposited by performing a single action on a control member provided on said accessory.

13. Apparatus according to claim 12, wherein the accessory comprises an annular cover for covering the top ends of the tubes for grasping and fitted with a plurality of elastic snap-fastener means designed to engage and clamp onto the ends of the tubes, and a control member formed by a push-button or a quarter-turn button, for example, mounted on the cover and designed to act on all of the snap-fastener means in order to release the ends of the tubes.

* * * * *

UNITED STATES PATENT AND TRADEMARK OFFICE
CERTIFICATE OF CORRECTION

PATENT NO. : 7,954,741 B2
APPLICATION NO. : 12/306073
DATED : June 7, 2011
INVENTOR(S) : Kunc et al.

It is certified that error appears in the above-identified patent and that said Letters Patent is hereby corrected as shown below:

Column 1,
Line 3, after the title and before the first paragraph, insert the following:

--CROSS REFERENCE TO RELATED APPLICATIONS

This application is a national stage application filed under 35 USC 371 of International Application No. PCT/FR2007/001094, filed June 28, 2007, which claims priority from French patent application 06 05944, filed June 30, 2006.

FIELD AND BACKGROUND OF THE INVENTION--.

Column 1,
After the paragraph ending at numbered line 32, insert the following subheading:

--SUMMARY OF THE INVENTION--;

Lines 41-42, "the apparatus being characterized in that tube cooling" should read --wherein tube cooling--.

Column 2,
After the paragraph ending at numbered line 34, insert the following subheading:

--BRIEF DESCRIPTION OF THE DRAWINGS--;

After the paragraph ending at numbered line 51, insert the following subheading:

Figure 1:
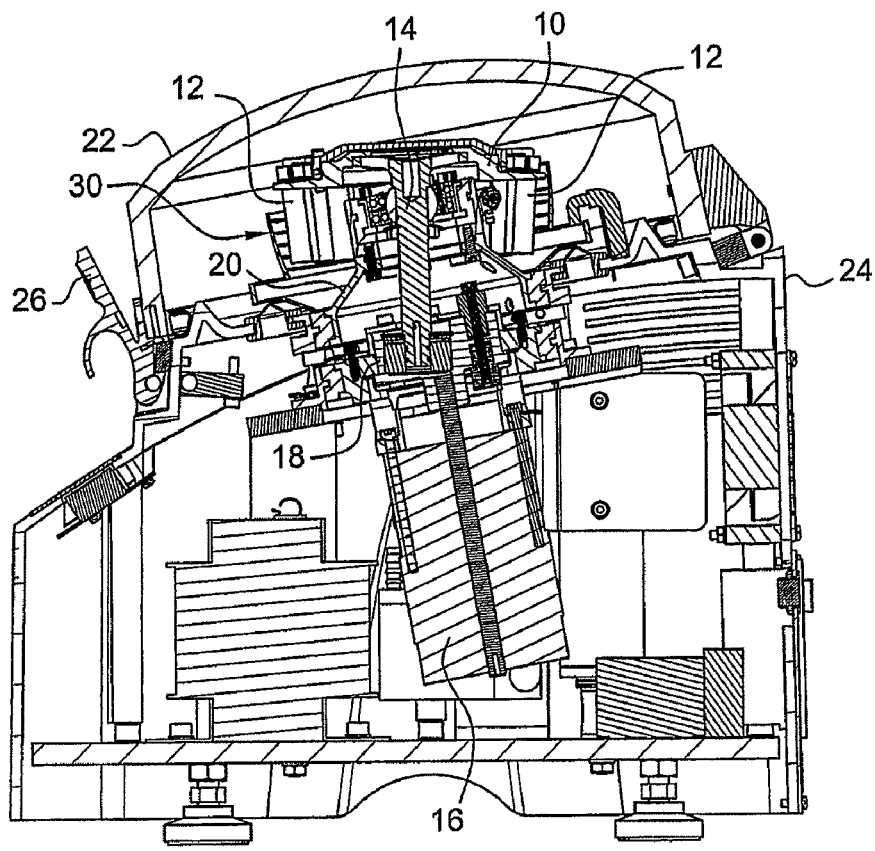
Figure 2:
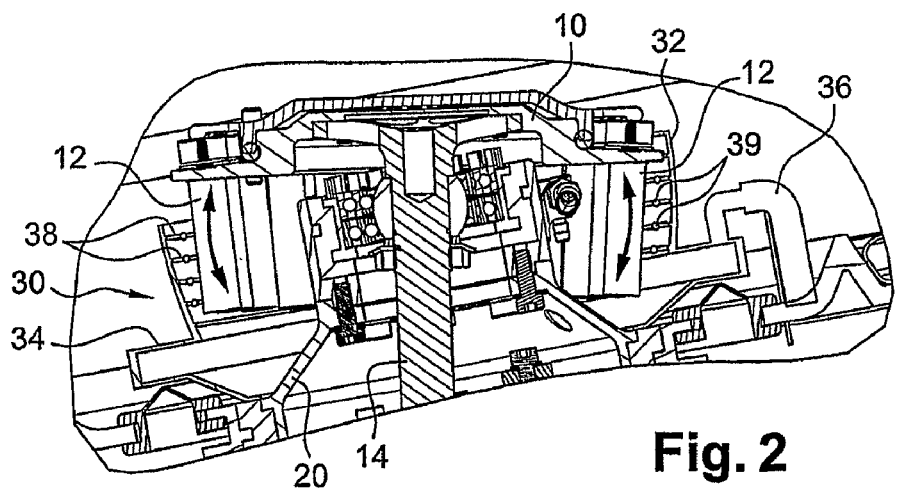
Figure 3:
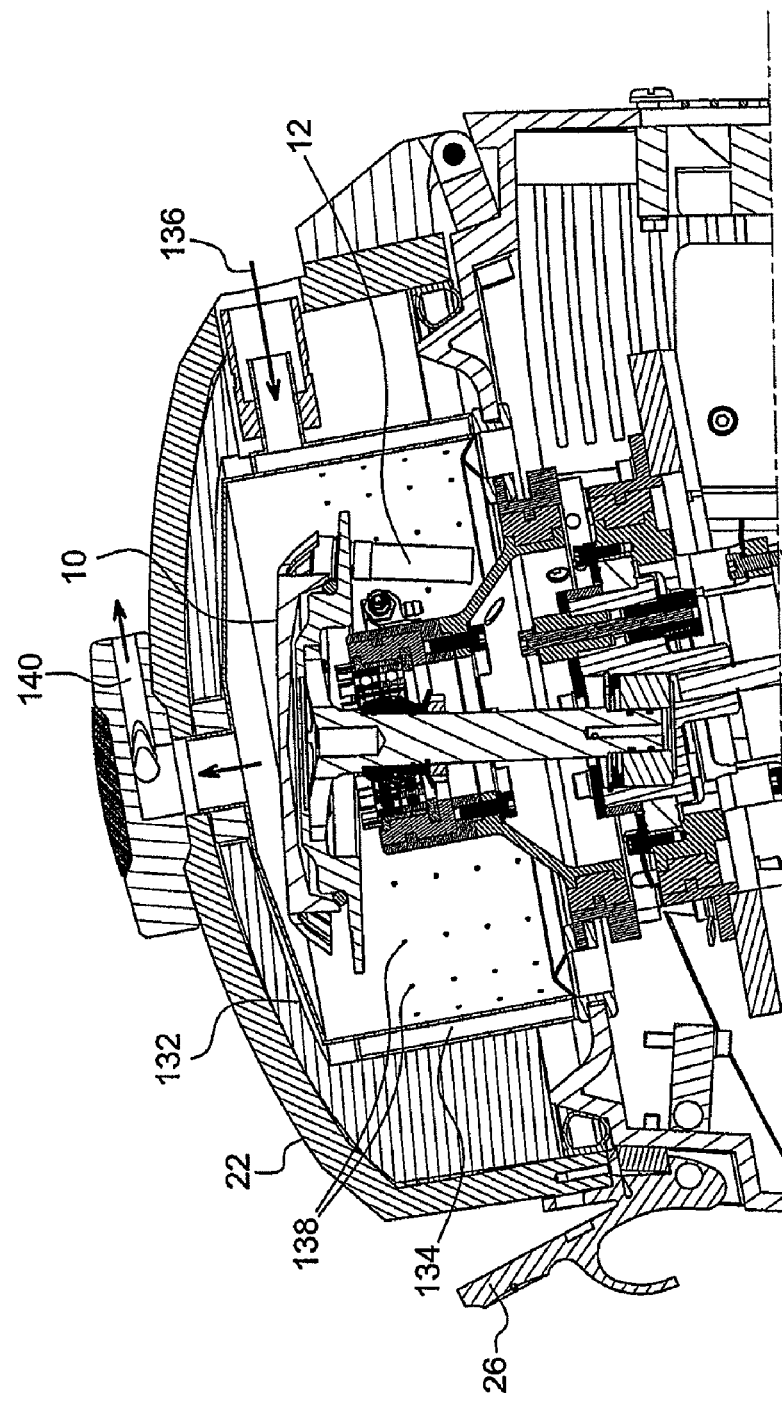
Figure 4:
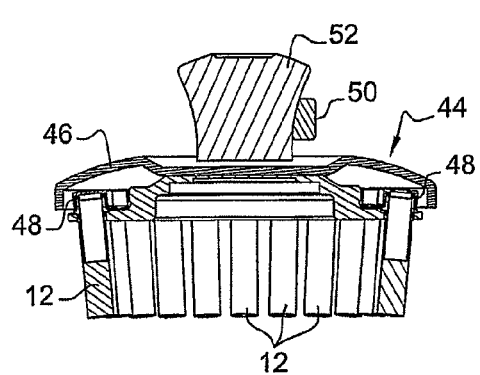
Figure 5:
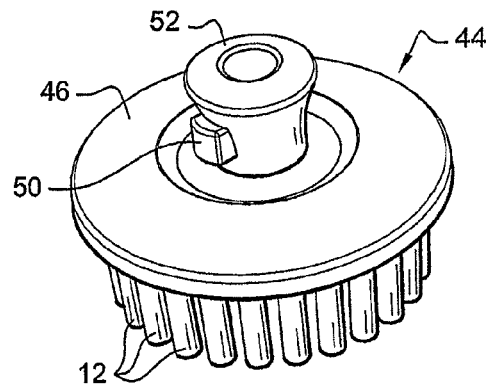
Figure 6:
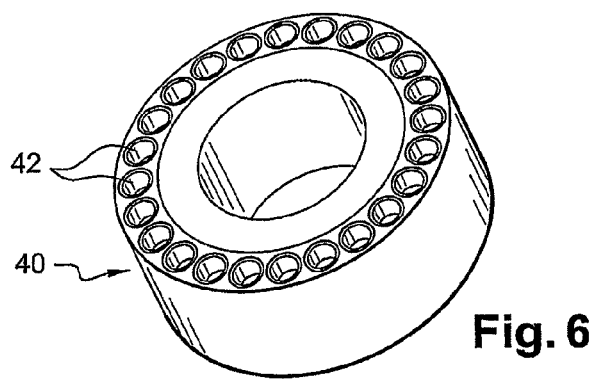
Figure 7A:
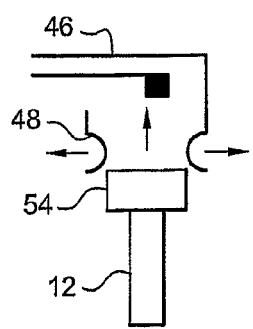
Figure 7B:
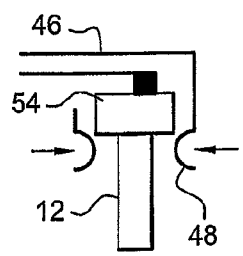
Figure 7C:
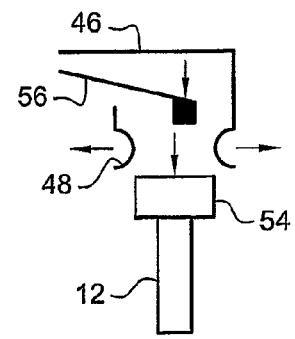

--DETAILED DESCRIPTION--.

Signed and Sealed this
First Day of May, 2012

David J. Kappos
*Director of the United States Patent and Trademark Office*